United States Patent [19]

Henke

[11] Patent Number: 5,558,652

[45] Date of Patent: Sep. 24, 1996

[54] INTRODUCER WITH RADIOPAQUE MARKED TIP AND METHOD OF MANUFACTURE THEREFOR

[75] Inventor: Bruce D. Henke, Deephaven, Minn.

[73] Assignee: B. Braun Medical, Inc., Bethlehem, Pa.

[21] Appl. No.: 318,951

[22] Filed: Oct. 6, 1994

[51] Int. Cl.⁶ ................................................ A61M 25/00
[52] U.S. Cl. ........................ 604/280; 604/256; 128/658
[58] Field of Search .......................... 604/96, 164, 256, 604/264, 280; 128/656–658

[56] References Cited

U.S. PATENT DOCUMENTS

| | | |
|---|---|---|
| 4,149,082 | 4/1979 | Haendle et al. . |
| 4,350,159 | 9/1982 | Gouda . |
| 4,471,777 | 9/1984 | McCorkle, Jr. . |
| 4,585,000 | 4/1986 | Hershenson . |
| 4,738,667 | 4/1988 | Galloway . |
| 4,795,463 | 1/1989 | Gerow . |
| 4,838,879 | 6/1989 | Tanabe et al. ................... 604/280 |
| 4,850,960 | 7/1989 | Grayzel ............................. 604/53 |
| 4,960,412 | 10/1990 | Fink ................................ 604/167 |
| 5,021,043 | 6/1991 | Becker et al. .................... 604/49 |
| 5,180,387 | 1/1993 | Ghajar et al. . |
| 5,203,777 | 4/1993 | Lee .................................. 604/280 |
| 5,415,636 | 5/1995 | Forman ............................ 604/101 |
| 5,425,709 | 6/1995 | Gambale .......................... 604/96 |

OTHER PUBLICATIONS

"Check-Flo II Blue Introducer Sets", brochure from Cook Incorporated, RCFRB1192.

*Primary Examiner*—Corrine M. McDermott
*Attorney, Agent, or Firm*—Joel D. Skinner, Jr.

[57] ABSTRACT

A medical vascular introducer of the type having an elongated hollow shaft, a distal portion of which is insertable into the body of a patient, wherein the improvement comprises a pair of radiopaque markers disposed at two longitudinally distinct positions on the exterior of the shaft, the markers being separated a predetermined longitudinal distance. Also disclosed is a marker design which is circumferentially discontinuous and consists of at least one marker segment and at least one void area.

20 Claims, 2 Drawing Sheets

5,558,652

INTRODUCER WITH RADIOPAQUE MARKED TIP AND METHOD OF MANUFACTURE THEREFOR

BACKGROUND OF THE INVENTION

1. Field of the Invention.

This invention relates to medical devices in general and, more particularly, to hemostasis introducer devices and methods of manufacture therefor. The hemostasis introducer provided by this invention is used as an ingress/egress point to the vascular system of a patient, for example, during angioplasty. The introducer seals the puncture to prevent leakage of blood therefrom. A radiopaque marked tip of the introducer allows the user to properly position the device within the vasculature and for calibration of related medical devices.

2. Background Information.

Various surgical procedures are performed by medical specialists such as cardiologists and radiologists, using percutaneous entry into a blood vessel or body cavity. Examples of such procedures include techniques to recanalize atherosclerotic blood vessels, such as balloon angioplasty, atherectomy or stent placement. Recently, both the types and number of procedures performed using the above mentioned percutaneous access to blood vessels have increased greatly.

These procedures generally involve the percutaneous puncture with a thin-walled needle into a blood vessel. Following this, a guidewire is placed through the needle into the blood vessel and the needle is withdrawn. An intravascular introducer or sheath of variable size, in combination with a tissue dilator, is then advanced over the guidewire, percutaneously, into the lumen of the blood vessel. The introducer is then used as an ingress/egress means during the procedure. Catheters, balloon devices, guidewires, stents filters and other medical devices may be inserted, manipulated and removed in and from the introducer. The placement of such catheters and other devices is typically monitored by a fluoroscope.

Introducers generally comprise a sheath, the proximal end of which is capped and sealed with an elastomeric gasket or valve. The gasket typically has an aperture through its center which seals against blood pressure in the body while allowing insertion or introduction of a catheter or stent through the gasket aperture, down the sheath, and into the blood vessel.

The marking of intravascular devices with radiopaque materials to indicate their position within the body is known. However, the particular materials and methods used for marking have various limitations. Specifically, the materials and methods are not optimally suited to the materials of which the introducers and sheaths are constructed. Additionally, prior art marker designs are at risk of failure due to differential expansion and contraction of the substrate and marker structures and compositions which commonly occurs during use. Finally, insofar as is known, no hemostasis introducer includes a marker that is useable to calibrate fluoroscopic equipment and the like, which are used to view introducer placement.

Despite the need in the art for an introducer and method of manufacture therefor which overcome the limitations and problems of the prior art, none insofar as is known has been proposed or developed. The present invention is specifically directed to overcoming all of the problems previously enumerated regarding the structure and performance of intravascular introducers and sheaths.

SUMMARY OF THE INVENTION

The apparatus of the present invention provides a medical vascular introducer of the type having an elongated hollow shaft, a distal portion of which is insertable into the body of a patient, wherein the improvement comprises a pair of markers disposed at two or more longitudinally distinct positions on the exterior of the shaft, the markers being separated a predetermined longitudinal distance, the markers further being constructed of a radiopaque material.

In an alternative embodiment, the improvement comprises at least one marker, preferably of a predetermined known width, disposed on the exterior of the shaft, the marker being constructed of a circumferentially discontinuous band of radiopaque material consisting of at least one marker segment and at least one void area.

A method of making a medical introducer as set forth above is also provided. The method comprises the steps of:

(a) providing an elongated, hollow tube constructed of a flexible polymeric material; and (b) depositing a radiopaque substance at least one predetermined location on an exterior surface of the tube via sputter coating to form a circumferentially oriented fluoroscopic marker band.

The benefits of this invention will become clear from the following description by reference to the drawings.

DESCRIPTION OF THE PREFERRED EMBODIMENTS

The apparatus of the present invention is used as an ingress/egress point to the vascular system of a patient during medical procedures such as angioplasty and other procedures, performed by cardiologists or radiologists. The introducer seals the puncture to prevent leakage of blood therefrom. In procedures such as angioplasty, where a balloon is introduced at the end of a catheter is used to expand a partially occluded artery, exacting placement is extremely important. A radiopaque marked tip of the introducer allows the user to properly position both the introducer and an extended medical device or devices within the vasculature and for calibration of the internally disposed size and position of such medical devices.

Figure 1:
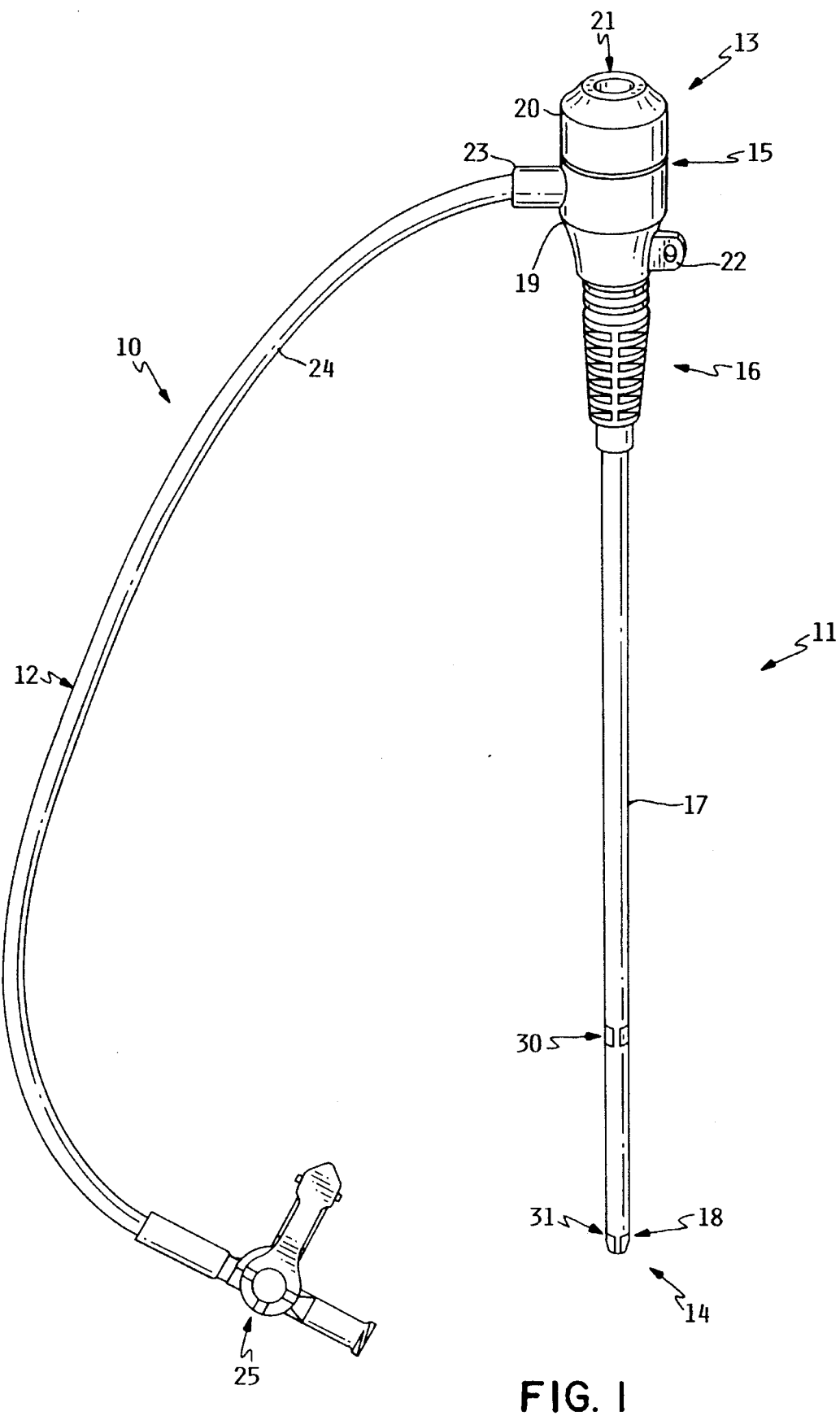
FIG. 1 is a perspective view of a hemostasis introducer with radiopaque marked tip of the present invention.

Referring to FIG. 1, the hemostasis introducer 10 of the present invention basically comprises an elongated, cylindrical body member 11 and an inlet/outlet tube member 12. The body 11 is approximately 6.75 inches (17 cm.) long and has proximal and distal ends 13 and 14. The tube 12 is approximately 8 inches (21 cm.) long and extends from the proximal end 13 of the body 11.

The body member 11 basically comprises a valve housing 15, a strain relief member 16, and a shaft 17. The valve housing 15 is a hollow, cylindrical structure disposed at the proximal end 13 of the body 11. The valve housing 15 is constructed of plastic such as polypropylene, polyurethane or polycarbonate. The shaft 17 is an elongated, tubular structure which extends linearly from the valve housing 15. The shaft 17 has a diameter between 3 and 20 French. The shaft 17 is preferably constructed fluorinated ethylene propylene (FEP) such as Teflon® or Neoflon® and is semi-rigid. Alternatively, the shaft 17 may be constructed of high density polyethylene (HDPE) or a similar substance. The shaft 17 is preferably non-radiopaque, but may alternatively be semi-radiopaque. This allows the practitioner to view, via fluoroscopy, the device being advanced through the shaft 17 of the introducer 10 during the medical procedure. The strain relief member 16 is disposed at the intersection of the valve housing 15 and the shaft 17. It accommodates the flexing of the shaft 17 that typically occurs during use and prevents it from separating from the valve housing 15. The distal end 14 of the shaft 17 has a taper 18. First or proximal and second or distal markers 30 and 31, respectively, are disposed at predetermined positions on the shaft 17. The structure and function of these markers 30 and 31 are discussed in detail below.

Figure 2:
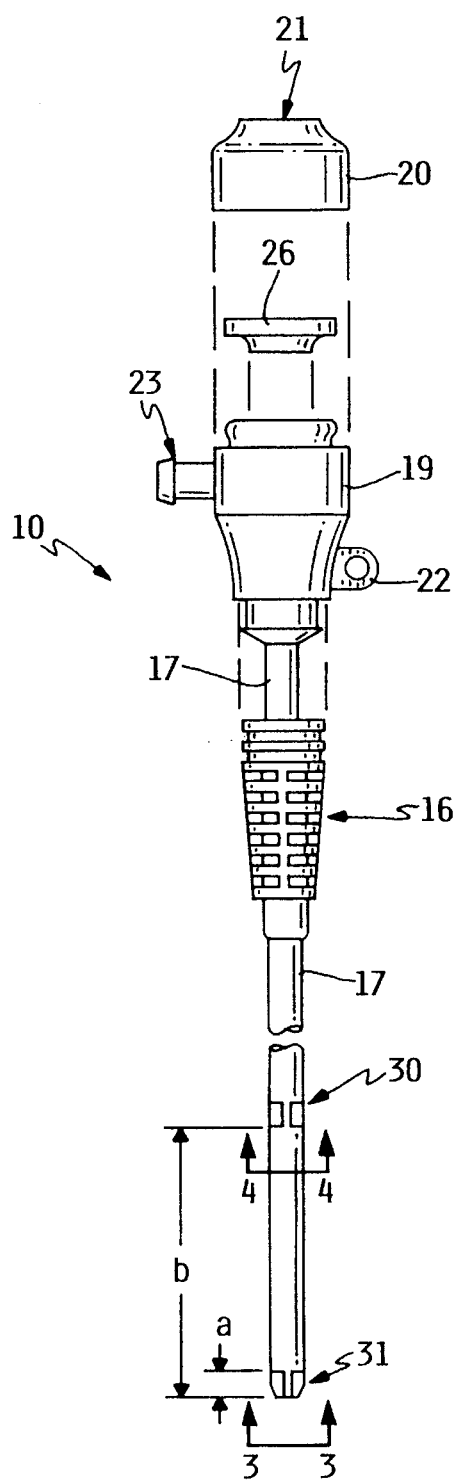
FIG. 2 is a side view of the hemostasis introducer.

The valve housing 15 is preferably of a design such as that shown in copending U.S. patent application Ser. No. 08/112,436, filed Aug. 26, 1993, owned by applicant's assignee, which is incorporated by reference herein. Referring also to FIG. 2, the valve housing 15 includes a base member 19, a cap member 20 and a valve 26. The base and cap members 19 and 20 enclose the valve or gasket 26, which is seated transaxially at their interface. The valve 26 is preferably constructed of an elastomeric material such as silicone or natural rubber, and has a self sealing slit (not shown) which permits passage of inserted medical devices and which also forms a leak-proof seal to prevent blood or other fluids in the patient's vascular system from exiting the introducer 10. The base and cap members 19 and 20 are preferably constructed and arranged to snap together, but may alternatively be connected via an adhesive or weld, or may be of a unitary one-piece design. The cap member 19 has a circular aperture 21 disposed at its distal end to permit passage of a medical device.

The inlet/outlet tube assembly 12 provides a means of adding or withdrawing fluids to and from the patient through the introducer 10. The inlet/outlet tube assembly 12 includes a flexible tube 24 which extends from a port 23 in the valve housing 15 and terminates at a stop cock valve 25. The port 23 opens to the hollow interior of the valve housing 15. The tube 24 is preferably constructed of a clear, flexible plastic. The valve 25 is of a design known in the art.

The valve housing 15 and the proximal portion of the shaft 17 of the introducer 10 remain on the exterior of the patient's body at all times, while the distal portion shaft 17 extends through a puncture in the skin surface, tissue, and vessel wall made by the user. A suture connector or loop 22 is disposed on the exterior of the valve housing 15. It may be used to maintain the introducer 10 in an operative position on the patient's skin surface for prolonged periods of time to permit continued access to the patient's vascular system.

The specific valve housing 15 and strain relief member 16 structures disclosed above may be modified consistent with the teachings of this invention. The important aspect of the invention is the provision of markers 30 and 31 of a particular structure and the method of manufacture for such markers 30 and 31. It is specifically within the purview of this invention to include tear-away type sheaths having a longitudinal score line which allows the shaft to be broken apart and removed prior to retracting the inserted medical device.

Figure 3:
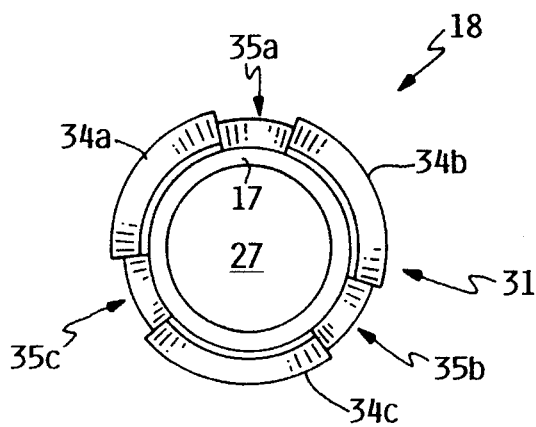
FIG. 3 is a crossectional view of the hemostasis introducer taken along line 3—3 of FIG. 2.
Figure 4:
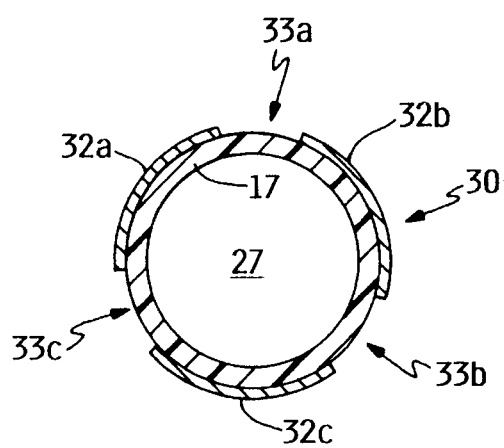
FIG. 4 is a crossectional view of the hemostasis introducer taken along line 4—4 of FIG. 2.

Referring to FIGS. 3 and 4, the markers 30 and 31 are disposed at predetermined locations on the exterior of the shaft 17. Placement of the markers 30 and 31 on the exterior of the shaft 17 reduces the risk of damage to the marker or dislodgment of marker material due to contact with the internally inserted device.

The second or distal marker 31 is disposed at the tapered terminal end 18 of the shaft 17. The marker 31 is a band of material having a predetermined width "a" of preferably 0.05–0.08 inches (0.12–0.20 cm.).

The first or proximal marker 30 is disposed at a predetermined location on the shaft, a distance "b" of preferably $0.787\pm0.020$ inches ($1.99\pm0.050$ cm.). The separation of the first and second markers 30 and 31 by a predetermined, known distance "b" allows the user to calibrate the fluoroscope, thus overcoming problems of parallax. Parallax is the apparent displacement of an object as seen from two different points not on a straight line with the object, and occurs during fluoroscopic viewing of a device or devices disposed in the patient's vasculature due to the elevation of the fluoroscope a certain distance above the body of the patient. Parallax may lead to inaccuracies in the placement of the devices in the patient's vasculature.

Importantly, the marker bands 30 and 31 are each circumferentially discontinuous and consist of preferably three (3) equidistantly spaced deposition segments 32a, b and c, and 34a, b, and c, which are separated by spaces 33a, b and c, and 35a, b and c, respectively. The discontinuous bands 30 and 31 allow the polymeric shaft 17 to expand, contract and flex without undue risk of breakage of the less flexible metallic marker bands 30 and 31. Expansion, contraction and flexing of the shaft can occur for example when an oversize device is inserted in the introducer 10. Breakage of the marker band 30 or 31 could lead to undesirable dislodgment of metallic material into the patient's vasculature. The discontinuous bands 30 and 31 also allow the breakage of tear-away sheaths along a scoreline oriented in the spaces 33 and 35.

The markers 30 and 31 are constructed of a radiopaque metallic material. Gold is used on shafts constructed of HDPE. Titanium, stainless steel, copper, gold, silver, platinum or a combination of such materials is used on shafts constructed of FEP. Importantly, the radiopaque material is deposited on the shaft 17 via a coating process, preferably sputter coating. This enables the radiopaque material to adhere to the shaft 17 substrate. HDPE and FEP substrates are very slippery and difficult to adhere to. The coating is of sufficient thickness to provide adequate radiodensity in the resultant fluoroscopic images.

In use, a puncture is made with a thin walled needle through the skin and into a blood vessel. Following this, a guidewire is placed through the needle into the blood vessel and the needle is withdrawn. A predetermined size of the intravascular introducer 10 is selected and then advanced over the guidewire, percutaneously, into the lumen of the blood vessel. The introducer 10 is then used as an ingress/egress means during the medical procedure. Catheters, guidewires and other devices may be inserted into, manipulated and removed from the introducer 10. The placement of such devices is typically monitored by a fluoroscope. Using the known distance between the first and second markers 30 and 31, the physician is able to properly calibrate the fluoroscope. The risk of failure of the markers 30 and 31 during normal usage is minimized by the apparatus of the present invention.

As many changes are possible to the embodiments of this invention utilizing the teachings thereof, the descriptions above, and the accompanying drawings should be interpreted in the illustrative and not the limited sense.

The invention claimed is:

1. A medical vascular introducer of the type having an elongated hollow shaft with proximal and distal portions, said distal portion being insertable into the body of a patient, wherein the improvement comprises at least one marker disposed on the exterior of said shaft, said at least one marker being constructed of a circumferentially discontinuous band of radiopaque material comprising at least two marker segments, said marker segments being circumferentially separated from each other by void areas of said shaft, whereby said void areas permit expansion and contraction of said radiopaque material with respect to said shaft.

2. A medical vascular introducer of the type having an elongated hollow shaft with proximal and distal portions, and a distal tip, the distal portion being insertable into the body of a patient, wherein the improvement comprises a pair of markers disposed at two longitudinally distinct positions on the exterior of the shaft, said markers being separated a predetermined longitudinal distance, said markers being constructed of circumferentially discontinuous bands of a radiopaque metallic substance consisting of three marker segments and three void areas.

3. The introducer of claim 2, wherein a first marker is disposed at the distal tip of the shaft and wherein a second marker is disposed proximally with respect to said first marker.

4. The introducer of claim 2, wherein said predetermined longitudinal distance is 0.787±0.020 inches.

5. The introducer of claim 2, wherein the shaft is constructed of FEP, and wherein said metallic substance is selected from the group of substances consisting of titanium, stainless steel, copper, gold, silver and platinum, said metallic substance being deposited by a coating process.

6. The introducer of claim 2, wherein the shaft is constructed of HDPE, and wherein said markers are constructed of gold deposited by a coating process.

7. The introducer of claim 2, wherein said marker bands have a width of 0.05–0.08 inches.

8. The introducer of claim 2, wherein the medical vascular introducer is a hemostasis introducer comprising the shaft, the shaft having a lumen, a housing disposed at a proximal end of the shaft, a valve disposed in the housing, transaxially with respect to the lumen of the shaft, and means to relieve strain between the shaft and the housing.

9. A medical vascular introducer of the type having an elongated hollow shaft with proximal and distal portions, and a distal tip, the distal portion being insertable into the body of a patient, wherein the improvement comprises at least one marker disposed on the exterior of the shaft, said marker being constructed of a circumferentially discontinuous band of radiopaque material consisting of three marker segments and three void areas.

10. The introducer of claim 9, wherein there are a pair of markers disposed at two longitudinally distinct positions on the shaft, said markers being separated a predetermined longitudinal distance.

11. The introducer of claim 10, wherein a first marker is disposed at the distal tip of the shaft and wherein a second marker is disposed proximally with respect to said first marker.

12. The introducer of claim 10, wherein said predetermined longitudinal distance is 0.787±0.020 inches.

13. The introducer of claim 9, wherein the shaft is constructed of FEP, and wherein said radiopaque is a metallic substance selected from the group of substances consisting of titanium, stainless steel, copper, gold, silver, and platinum, said metallic substance being deposited by a coating process.

14. The introducer of claim 9, wherein the shaft is constructed of HDPE, and wherein said marker is constructed of gold deposited by a coating process.

15. The introducer of claim 9, wherein said at least one marker segment has a width of 0.05–0.08 inches.

16. The introducer of claim 9, wherein the medical vascular introducer is a hemostasis introducer comprising the shaft, the shaft having a lumen, a housing disposed at a proximal end of the shaft, a valve disposed in the housing, transaxially with respect to the lumen of the shaft, and means to relieve strain between the shaft and the housing.

17. A method of making a medical introducer comprising the steps of:

(a) providing an elongated, hollow tube constructed of a flexible polymeric material; and (b) depositing a radiopaque substance at at least one predetermined location on an exterior surface of said tube via sputter coating to form a circumferentially oriented fluoroscopic marker band consisting of three marker segments separated by three void areas.

18. The method of claim 17, wherein a pair of marker bands are deposited at two longitudinally distinct positions on the shaft, said marker bands being separated a predetermined longitudinal distance.

19. The method of claim 17, wherein the shaft is constructed of FEP and wherein said radiopaque substance is a selected from the group consisting of titanium, stainless steel, copper, gold, silver, and platinum.

20. The method of claim 17, wherein the shaft is constructed of HDPE and wherein said radiopaque substance is gold.

* * * * *